United States Patent [19]

Spani et al.

[11] Patent Number: 5,463,906
[45] Date of Patent: Nov. 7, 1995

[54] INTERCHANGEABLE DISPOSABLE ACOUSTIC FOR USE WITH AN ULTRASONIC FLOWMETER, PARTICULARLY DURING EXTRACORPOREAL MEASUREMENT OF BLOOD FLOW

[75] Inventors: Wayne M. Spani; William S. Kemper, both of San Diego, Calif.

[73] Assignee: Triton Technology, Inc., San Diego, Calif.

[21] Appl. No.: 184,992

[22] Filed: Jan. 24, 1994

[51] Int. Cl.[6] .................................................... G01F 1/66
[52] U.S. Cl. ................... 73/861.27; 73/861.28
[58] Field of Search .................. 73/861.25–861.31; 128/661.1, 662.01

[56] References Cited

U.S. PATENT DOCUMENTS

| | | | |
|---|---|---|---|
| 3,050,997 | 8/1962 | Lake | 73/861.27 |
| 3,575,050 | 4/1971 | Lynnworth | 73/861.27 |
| 3,964,309 | 6/1976 | Husse et al. | 73/861.28 |
| 4,144,752 | 3/1979 | Lolk | 73/861.28 |
| 4,325,262 | 4/1982 | Meisser | 73/861.28 |
| 4,425,804 | 1/1984 | Mount et al. | 73/861.28 |
| 4,480,486 | 11/1984 | Meisser et al. | 73/861.28 |
| 5,179,862 | 1/1993 | Lynnworth | 73/861.28 |
| 5,243,863 | 9/1993 | Gill | 73/861.28 |

*Primary Examiner*—Richard Chilcot
*Assistant Examiner*—Elizabeth L. Dougherty
*Attorney, Agent, or Firm*—William C. Fuess

[57] ABSTRACT

An inexpensive disposable plastic flow body interchangeably flow connects in line a conduit flowing fluid, and also, concurrently, acoustically connects to one or more ultrasonic transducers, so as to serve as an acoustic chamber for use with an ultrasonic flowmeter in the measurement of fluid flow velocity and/or volume. The flow connection is preferably accomplished by plugging, preferably by inserting nozzles into surgical tubing. The external ultrasonic transducer(s) is (are) normally connected under pressured contact, typically under spring forces which are preferably of external origin. Acoustic-coupling elements in the walls of the acoustic chamber serve to match the acoustic impedance of the flow body to acoustic impedance of blood. The disposable plug-connected flow body is particularly safe, sterile and convenient for extracorporeal ultrasonic blood flow measurement.

20 Claims, 5 Drawing Sheets

INTERCHANGEABLE DISPOSABLE ACOUSTIC FOR USE WITH AN ULTRASONIC FLOWMETER, PARTICULARLY DURING EXTRACORPOREAL MEASUREMENT OF BLOOD FLOW

BACKGROUND OF THE INVENTION

1. Field of the Invention

The present invention generally relates to ultrasonic fluid flow measurement, and to ultrasonic flowmeters.

The present invention more specifically relates to a disposable acoustic chamber useable with a pre-existing ultrasonic flowmeter in the extracorporeal measurement of the flow of blood, or in the measurement of the flow of other liquids.

2. Description of the Prior Art 2.1 Ultrasonic Fluid Flow Measurement, and Flowmeters The use of ultrasonic flowmeters of both the transit time and Doppler types to measure the flows of fluids through conduits is well known. Ultrasound in the high frequency range from 100 KHz to 20 MHz, and more commonly in the range from 1 MHz to 20 MHz, is typically used. The ultrasound may be transmitted continuously by a Continuous Wave (CW) ultrasonic flowmeter, or in bursts by a pulsed Doppler ultrasonic flowmeter.

There are two common ultrasonic fluid flow measurement techniques. A transit time technique measures the difference in the transit times of sound projected upstream and downstream through a flowing fluid. This time difference is a function of that component of the vector velocity of fluid flow which is located along the ultrasonic path. The actual ultrasonic path may be diagonally transverse to, or coaxial with, the fluid flow vector. A transit time ultrasonic flowmeter is primarily sensitive to volumetric flow.

In Doppler ultrasonic fluid flow measurement ultrasound is transmitted in either an upstream or a downstream direction through a flowing fluid. The ultrasound is scattered or reflected by particles or bubbles that are suspended in the flowing fluid, and which are moving with the same velocity and direction as does the fluid. A portion of the returned ultrasound is detected, and the Doppler frequency shift of this returned ultrasound is an indication of the flow of the fluid, and more particularly of the velocity spectrum of the flow of the fluid. From this indicated velocity the volume of fluid flow can be calculated when the cross-sectional area of the flow conduit is known.

The detection of Doppler frequency shifted ultrasound sometimes transpires by, and in, the same ultrasonic transducer which initially projected the ultrasound sound in a manner similar to sonar. Sometimes separate transmitting and receiving transducers are used, particularly for continuous wave (CW) Doppler embodiments.

The amount of the Doppler frequency shift undergone by the reflected ultrasound is really a double Doppler frequency shift: one Doppler frequency shift being incurred on the outward path (before reflection) and another Doppler frequency shift being incurred by the reflected signal along its return path. The total amount of the Doppler frequency shift is a function of that component of the vector velocity of fluid flow which is located along both legs of the ultrasonic path. The ultrasonic path is normally at a known angle to the fluid flow vector, typically at a 45° angle. Accordingly, the actual fluid velocity v is inversely proportional to the cosine of the angle between the ultrasonic axis and the flow axis (cos θ) and to the frequency of the ultrasound $f_o$, and is directly proportional to the detected frequency shift ($\Delta f$) and to the velocity of sound (c) in the fluid medium. This may be mathematically stated as:

$$v = \frac{(\Delta f)c}{2 f_o \cos \theta}$$

Both the transit time and Doppler ultrasonic fluid flow measurement techniques have previously been used to monitor the flow of various fluids through assorted pipes, conduits, and lumens, as well as the flow of blood through blood vessels.

2.2 Electromagnetic Fluid Flow Measurement, and Flowmeters

Meanwhile, it is also known to use flowmeters of the electromagnetic type to measure the flow of fluids, including the flow of blood. In use of an electromagnetic flowmeter for measuring fluid flow an electrically conductive liquid is passed through a conduit—typically either a tube or blood vessel—at right angles to a magnetic field that is typically established by electromagnets. The electrically conductive flowing fluid serves as a moving conductor in the magnetic field, and, by the laws of physics, induces an electromagnetic force (EMF) in a direction perpendicular to the applied magnetic field. This EMF can be measured as a voltage differential between electrodes that are positioned diametrically oppositely across the conduit along a diameter that extends perpendicularly to the lines of magnetic flux. The voltage generated is proportional to the volume rate of blood flow. Blood may suitably serve as an electrically conductive fluid.

2.3 Challenges of Extracorporeal Blood Flow Measurement, and Previous Electromagnetic Flowmeters Used in Extracorporeal Blood Flow Measurement The flow of blood in a live human patient must be measured and/or monitored upon certain occasions, such as during the connection of an artificial heart and lung machine into the patient's circulatory system. The patient's blood flow is most conveniently and safely so measured extracorporeally (outside the body). Historically, and although acoustic flowmeters have been known for over forty years, the extracorporeal measurement of blood flow has typically transpired by use of electrical equipments, typically electromagnetic flowmeters. The use of electromagnetic flowmeters has possibly been related to the frequent presence of other electrical, electronic, and electromagnetic equipments during surgical procedures, such as open heart surgery, that require the extracorporeal measurement of blood flow and blood circulation. More recently ultrasonic flowmeters have also come into use for the extracorporeal measurement of blood flow.

Progress in facilitating the somewhat cumbersome connection of a patient for extracorporeal blood flow measurement has been made only for electromagnetic blood flow measurement, and then only to a limited extent. Before the invention of the partially-disposable in-line electromagnetic flow measurement transducer shown and described in U.S. Pat. No. 4,195,515 to Smoll, the required sensor assembly of an electromagnetic flowmeter used to perform an extracorporeal blood flow measurement or monitoring was normally assembled as one composite unit. The assembled sensor assembly typically included a precision-aligned (i) flow tube, (ii) electrodes and (iii) magnet. The assembled, unitary, sensor assembly was expensive and difficult to sterilize after each use. Separate sensor assemblies were required for each flow channel, or flow point, to be measured. If measurements were to transpire in differently sized flow lines then differently sized sensor assemblies were required.

The in line electromagnetic flow measurement transducer shown and described in U.S. Pat. No. 4,195,515 to Smoll divided the previous composite electromagnetic flowmeter sensor assembly into two separate, physically and electrically plug-connected, parts. One part was a tubular member having electrode sensors. The tubular member readily and easily flow connected to elastomeric surgical tubes through nozzle features. It was typically so inexpensive as to be disposable. Alternatively, the tubular member could be readily and easily interchanged and sterilized by conventional techniques.

The other part of Smoll's composite sensor assembly contained the relatively more expensive magnet used to generate the required magnetic field. When the two parts were physically and electrically quick-connected to each other by plugging, they formed the complete sensor assembly suitable for use with an electromagnetic flowmeter. A number of differently-sized first-part tubular members could each be used with the same second-part magnet member as best suited flow measurements taken at different points, and/or in differently sized flow lines.

2.4 Difficulties With the Use of In Line Electromagnetic Flow Transducers, and Electromagnetic Flowmeters, During Extracorporeal Blood Flow Measurement A first problem with the existing use of electromagnetic flowmeters in extracorporeal blood flow measurement is that an electromagnetic flowmeter commonly incurs an offset voltage, i.e. some voltage may be generated between the electrodes even when no fluid is flowing. This offset voltage typically drifts over time. To account for this drifting offset voltage, an electromagnetic flowmeter is typically zeroed and re-zeroed, by adjustment of its scale or otherwise, so as to properly read a zero flow when no flow is, in fact, present.

This offset, and necessary zeroing and re-zeroing, presents two problems during extracorporeal blood flow measurement. First, it is seldom convenient to stop, or re-stop, blood flow to a patient for which blood flow is being measured, or monitored, in order to zero, or re-zero, the flowmeter. Second, the offset may drift in an unpredictable manner due to uncontrolled changes in the environment of, and between, the electrodes; most notably changes in the conductance of the blood and/or changes in electrode impedance due to chemical action over time.

Previous electromagnetic blood flow measurements have generally been typically sufficiently accurate so that the general adequacy, and the continuance, of the circulation of blood in an patient may be monitored. However, because of a drift in the precision of measurement, electromagnetic blood flow measurement has generally lacked such accuracy as would permit minor trends and/or perturbations in blood flow to be observed. Because these trends and/or perturbations, howsoever minor, may be important relative to the surgical procedures being performed, it is best if they are promptly, clearly and unambiguously detected.

By comparison, ultrasonic flowmeters do not suffer from these limitations. Offsets in ultrasonic flowmeters are much lower in magnitude, and ultrasonic flowmeter are more stable with time than are electromagnetic flowmeters. Any such calibration as needs be performed on an ultrasonic flowmeter requires no alteration, nor any bypass, of the blood flow.

A second problem with the use of electromagnetic flowmeters in extracorporeal blood flow measurement is that such flowmeters require direct, intimate, electrically-conducting contact between metal electrodes and the fluid blood. This contact is undesirable in that reaction chemistry, contamination, flow path disruption or perturbation, and/or blood clotting may occur.

Conversely, and by comparison, there need be no direct contact between the transducers of an ultrasonic flowmeter and the fluid, or blood, for which flow is measured. Medical grade plumbing such as surgical hose typically serves as a conduit for the flow of blood outside a patient's body. The walls of the conduit are typically seamless and smooth, and without substantial chemical or physical differentiation from region to region. The conduit walls are typically non-thrombogenic, and do not induce blood clotting.

Ultrasonic transducers are disposed to the exterior of the conduit, and transmit sound through the conduit walls as well as through the flowing fluid blood. In this location the transducers never come into direct contact with the blood, nor with anything that is within the blood. The conduit through which blood flows during ultrasonic blood flow measurement may be a blood vessel itself as well as, typically, plastic surgical tubing which is flow-connected to a blood vessel.

2.5 A Previous Attempt to Use An Ultrasonic Flowmeter During Extracorporeal Blood Flow Measurement With increasing use of ultrasonic flowmeters of both the transit time and Doppler types for measuring blood flow within the body of a live patient or animal (i.e., in vivo), it has previously been contemplated to also use ultrasonic flowmeters for measuring the flow of blood outside of the patient's or the animal's body. In order to so measure extracorporeal blood flow, (i) one or more ultrasonic transducers must be ultrasonically coupled to a flow of blood outside the patient's body, and (ii) an ultrasonic path must be established and defined through the flowing blood.

One previous system for realizing both requirements is the SNAP-ON FLOW MEASUREMENT SYSTEM of Lynnworth described in U.S. Pat. No. 5,179,862. Although Lynnworth is primarily concerned with industrial fluid flow measurement applications, one embodiment of his system contemplates a conduit, normally a surgical hose, for channeling a flow of blood. The surgical hose is attached to a support block that also serves to mount one of more ultrasonic transducers. The transducers are held in positions so that they both launch and receive ultrasound signals along a precisely defined path through the flowing fluid. The path may be either be axial along the conduit and along the path of the flowing fluid therein—as is common for smaller conduits channeling lessor blood flows—or—as is common for larger conduits channeling more voluminous blood flows—obliquely across the conduit. The oblique paths include paths crossing the conduit more than one time in a zig-zag fashion with multiple acoustic reflections.

In the Lynnworth system channels of predetermined configuration within the support block—which block and channels may both be physically sizable—hold the conduit in acoustic contact and precise alignment with ultrasonic transducers that are located externally to the conduit. This acoustic coupling is difficult and laborious to establish, and occasionally of poor quality. The setup of the conduit (the surgical hose) and the ultrasonic transducers normally requires the attention of a skilled technician, especially if critical reliance is to be made on the flow measurement results during surgery.

In the Lynnworth system ultrasonic waves must, by definition, penetrate the walls of the conduit (the surgical hose) at least twice (once in each of the transmit and receive directions), thereby presenting an undesirable source of reduction in ultrasonic signal due to attenuation and refraction.

Accordingly, it would be desirable if some improvement could be made to the easy, inexpensive, accurate, safe, and convenient use of an ultrasonic flowmeter (of either the transit time of Doppler types) during extracorporeal blood flow measurement.

SUMMARY OF THE INVENTION

The present invention contemplates an interchangeable disposable hollow flow body having and defining an acoustic chamber, the hollow flow body being usable with an ultrasonic flowmeter during the extracorporeal measurement of blood flow.

In one of its embodiments the invention is contained in a replaceable and interchangeable hollow flow body device for use with an ultrasonic flowmeter having at least one ultrasonic transducer. The hollow flow body has and defines an internal flow chamber having two end openings. Both the hollow flow body its open-ended chamber are preferably generally elongate in shape, and are typically in the substantial form of a tube having a longitudinal axis. The typically tubular flow body is normally several centimeters long, and a centimeter or so in thickness.

The tubular flow body having a longitudinal axis need not be perfectly straight. Indeed, it is typically bent. Commonly a central region of the tubular flow body is substantially straight along the flow body's longitudinal axis. However, both end regions of the elongate flow body commonly veer away from this axis, typically at angles from 30°–90°, and more typically at an angle of approximately 45°. The end regions of the tubular flow body do not have to veer away, or deviate, from the substantially straight central section of the flow body at the same angle, nor in the same plane, nor even in the same direction. Commonly, however, the hollow tubular flow body is roughly symmetrical about an imaginary plane perpendicularly bisecting its longitudinal axis at the center point thereof, and forms a substantial shape of the lip of a smiling mouth.

The cross-section of the exterior of the hollow tubular flow body perpendicular to its longitudinal axis can be, but need not be, the same, or even substantially the same, as the cross-section of its interior chamber perpendicular to the same axis. In one preferred embodiment the exterior cross-section of the hollow flow body is square while the cross-section of its interior chamber is circular. The exterior of the flow body is accordingly easy to grasp with the fingers while its interior chamber is smooth and featureless, and without obstruction to the flow of blood.

The hollow flow body is (ii) made of sound-conducting material. It is preferably (iii) disposable.

The hollow flow body is adapted to be both (i) flow-connected in line a conduit flowing fluid blood and, separately but concurrently, (ii) acoustically-connected to the ultrasonic transducer(s) of an acoustic flowmeter. Fluid blood flows through the interior chamber of the hollow flow body by virtue of the flow connection of the flow body in line a conduit flowing blood. Meanwhile, the flow body has and presents one or more exterior surfaces where it is pressured into contact with a corresponding one or more ultrasonic transducers of an acoustic flowmeter.

The fluid blood flows within the interior chamber of the hollow flow body in such a position, along such a path, and in such proximity, relative to the ultrasonic transducer(s) of the acoustic flowmeter that the fluid flow within the flow body may be sensed by the ultrasonic transducer(s), and by the ultrasonic flowmeter.

There is a conflict between (i) establishing a low-loss, non-refracting, arrow-straight acoustic path through the flowing fluid blood within the interior chamber of the hollow flow body and (ii) simultaneously preserving a smooth and featureless interior wall to the chamber. This is because the acoustic path must pass through the flowing blood over a sufficient distance, and at a sufficient angle, so that the blood flow can perturbate the ultrasound sufficiently to permit flow to be measured. This means that the acoustic path must basically lie along, or be at but a slight angle to the fluid flow vector. Because the one or more ultrasonic transducers are external to the hollow flow body, and to its interior chamber which establishes the local direction of the fluid flow vector, it is obvious that either (i) the ultrasonic transducer(s) must be oriented, and the ultrasound propagated, obliquely across the chamber and across the fluid flow therein, or (ii) the chamber must be bent so as to pass in front of the transducer(s) so that the fluid blood flows perpendicularly or substantially perpendicularly relative thereto. In either case the ultrasound must pass twice pass through walls of the chamber in a path that is not perpendicular to these walls, making that the ultrasound is undesirably refracted.

If, on the other hand, the chamber walls are perpendicular to the acoustic vector (and parallel to the plane(s) of the transducer(s)) so as to minimize thereby any undesirable acoustic refraction, then they must also present angular surfaces to the flowing blood. Small eddies or whirlpools of blood forming near these non-smooth, angular, features may undesirably damage the blood cells and, in extreme conditions, induce clots.

If, on the other hand, the interior walls of the chamber are smooth and featureless, as is desired for blood flow, then they are in portions necessarily oblique to the vector of acoustic propagation (i.e., non-parallel to the plane(s) of the transducer(s)), and are thus causative of undesirable acoustic signal refraction and signal loss.

The present invention solves this challenge to establishing a low-loss, non-refracting, arrow-straight acoustic path through a smooth and bending, almost serpentine, path of flowing fluid blood within the interior chamber of the hollow flow body. In simplistic terms, the present invention realizes (i) an acoustic path that is effectively straight and non-refracting, simultaneously with (ii) a flow path, regionally intersecting the acoustic path, that bends. The present invention solves these contradictory requirements by use of one or more acoustic-coupling bodies, or acoustic transformers, in permanent locations inside the flow body. The acoustic-coupling bodies are located in positions proximately to the walls of the flow chamber, or even so as to form portions of these walls. The acoustic-coupling bodies have an acoustic impedance similar to fluid blood, which is a different acoustic impedance that of the plastic from which the bulk of the flow body is normally constructed. According to this matching acoustic impedance, an acoustic signal will pass through an interface between an acoustic-coupling element and fluid blood without substantial refraction or reflection regardless that an angle between the acoustic vector and this interface (the wall(s) of the flow chamber) is not a right angle.

An acoustic-coupling element in accordance with the present invention is commonly made of urethane elastomer in the substantial shape of a wedge. A first surface of the wedge, which may be imbedded within the flow body for purpose of physical and chemical protection, is positioned substantially perpendicular to the acoustic vector and parallel to the plane(s) of the ultrasonic transducer(s). A second surface of the wedge, which surface is at an angle and is typically at about a 45° angle to the first surface, may again be imbedded within the flow body for purpose of physical and chemical protection. This second wedge surface is substantially parallel to a region of the wall of the flow body's interior chamber. The second wedge surface may even constitute the portion of the wall of the flow body's chamber.

This wall portion is smooth and contiguous with surrounding wall regions, making thereby a smooth flow path for the blood. Notably, however, this wall portion is at an angle, and non-perpendicular, to the acoustic vector. Nonetheless to so being at an angle to the acoustic vector, no appreciable undesirable acoustic refraction will occur at the oblique interface of this wall portion because the acoustic impedances on both sides of the interface—the acoustic impedance of the wedge-shaped body and of the fluid blood—are matched. Accordingly, the conflict in simultaneously establishing a low-loss, non-refracting, arrow-straight acoustic path through a smooth and featureless bending path within a walled chamber flowing fluid blood is overcome.

In detail, the hollow flow body is flow-connected in line a conduit flowing fluid blood through, and by, certain flow connection features. The preferred flow connection features are two plug adapters, and are more preferably two nozzles. The connection features, or plug adapters, or nozzles permit the hollow flow body to be temporarily reversibly connected in line the conduit flowing fluid blood. The conduit is typically a standard elastomeric surgical hose. The flow body is flow connected in line a fluid blood flow within this hose at any desired location by the simple and easy and process of simply cutting the hose and sliding each severed end thereof over a corresponding one of the two nozzles.

The hollow flow body is separately acoustically connected to one or more ultrasonic transducers of an acoustic flowmeter through, and by, certain acoustic connection features. The one or more acoustic connections is (are each) normally made at and along an exterior surface, and more typically at and along a substantial exterior surface, of the hollow flow body itself. The exterior surface(s) serve to make acoustic connection(s) to ultrasonic transducer(s) that is (are) located in and held by an external member, or mechanism. This external member, or mechanism, has and defines a cavity that is of complimentary size and shape to the three-dimensional structure of the flow body. (This cavity within the external member is completely separate from, and independent of, the chamber that is within the hollow flow body.)

At least one ultrasonic transducer is held upon an interior wall of the external member's cavity. The three-dimensional portion of the flow body is reversibly inserted into the cavity, normally by a simple plugging process, so that the at least one ultrasonic transducer is placed into tight pressured contact with the flow body, forming thereby a good, low-loss, acoustic connection. Good acoustic connection between the at least one transducer and the flow body residing within the cavity of the external member may be, and preferably is, aided and abetted by springs or latches. The springs or latches force a moveable potion, preferably a sliding portion, of the external member against the flow body, much in the manner of a clamp (in rudimentary form) or the locking bolt of a firearm (in more sophisticated form). The force-providing springs or latches serve to hold the transducer and the flow body tightly together in pressured contact. The springs and/or clamps can be retracted, and the acoustic connection(s) is (are) can easily be reversed (as were the flow connections).

The flow body is preferably made of sound-conducting material that is both (i) capable of being sterilized and (ii) inexpensive. The flow body is preferably molded from plastic. The preferred plastic flow body is both (i) delivered into service sterilized, and (ii) economically discarded after use.

The same flow body is suitable for use with either (i) one single ultrasonic transducer during extracorporeal Doppler acoustic blood flow measurement, or with (ii) two ultrasonic transducers during extracorporeal transit time acoustic blood flow measurement.

When the flow body is used during transit time acoustic fluid flow measurement it is acoustically connected—concurrently with its flow connection to a conduit flowing fluid—to each of two ultrasonic transducers. So acoustically- and flow-connected, the flow body serves to flow-conduct fluid in its interior chamber (i) between the pair of ultrasonic transducers, (ii) along a path so that a component of a fluid flow velocity vector is coupled to the ultrasonic transducers, and (iii) at a sufficient proximity to each of the pair of ultrasonic transducers, as permits the velocity of fluid flow within the chamber to be sensed by a transit time ultrasonic technique. The flow chamber is preferably elongate, and is typically several centimeters in length. The pair of ultrasonic transducers are preferably positioned and held by a mechanism at locations exterior to the flow body, in line with the opposite ends of its elongate chamber, and along the chamber's main axis and the vector of the fluid flow transpiring therein. In this position of the ultrasonic transducers a straight-line acoustic path is established from a first one of the transducers, through a sound-conducting wall of the flow body, through the fluid flowing within the flow chamber, through the sound conducting wall of the flow body, and to the remaining one of the transducers. The ultrasonic transducers so positioned and acoustically connected admirably serve to measure the velocity of fluid flow in the flow chamber by the transit time technique.

When the same flow body is used for Doppler ultrasonic fluid flow measurement then, concurrently with its flow connection to a conduit flowing fluid, it is typically acoustically connected to just one ultrasonic transducer (although it can be connected to more than one such transducer, see above). When so acoustically-and flow-connected, the flow body serves to flow-conduct fluid in its interior chamber (i) in a position opposite the ultrasonic transducer, (ii) along a path so that a component of a fluid flow velocity vector is coupled to the ultrasonic transducer, and (iii) at a sufficient proximity to the ultrasonic transducer, as permits the velocity of fluid flow within the chamber to be sensed by the Doppler acoustic technique. An ultrasonic path is established from the ultrasonic transducer, through a sound-conducting wall of the flow body, to and from the fluid that is flowing within the chamber, back through the sound-conducting wall of the flow body, and to the ultrasonic transducer. In this position the transducer admirably serves to measure the velocity of fluid flow within the flow chamber by the Doppler acoustic technique.

These and other aspects and attributes of the present invention will become increasingly clear upon reference to the following drawings and accompanying specification.

DESCRIPTION OF THE PREFERRED EMBODIMENT

The present invention is embodied in an interchangeable disposable hollow flow body having and presenting (i) an acoustic chamber, (ii) two tubing connectors for flow connecting to a conduit flowing fluid, and (iii) one or more acoustic connection features for acoustically connecting to at least one, and potentially several, ultrasonic transducers. The flow connection, and the separate acoustic connection(s) to the one or more ultrasonic transducers, are both (all) realized concurrently, normally by a simple manual plugging action.

Figure 1:
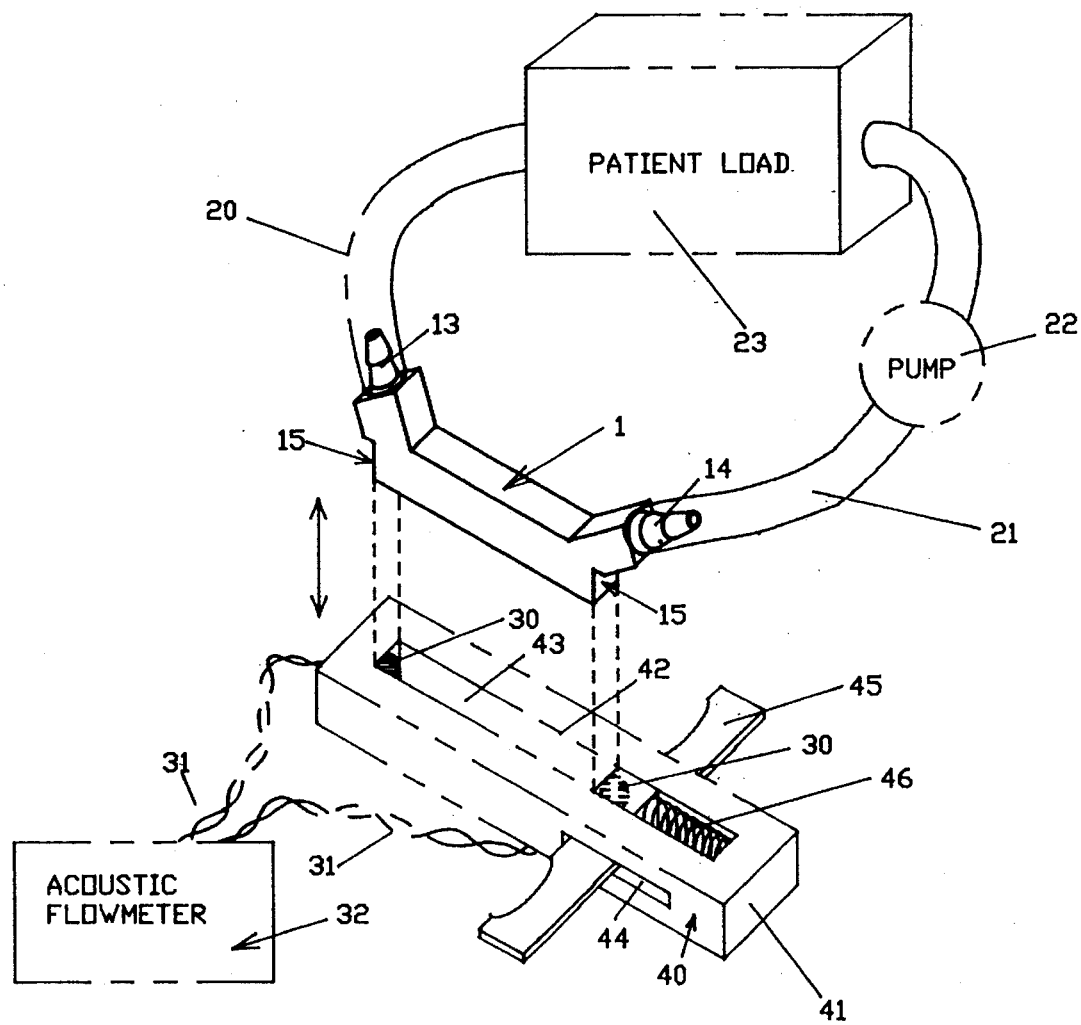
FIG. 1 is a diagrammatic view of a preferred embodiment of an interchangeable disposable hollow flow body, having and defining an ultrasonic flow chamber, in accordance with the present invention; the embodiment being diagrammatically shown in use with an ultrasonic flowmeter of either the Doppler or transit time types particularly during an extracorporeal measurement of blood flow.

An exemplary hollow flow body of the present invention for use with an ultrasonic flowmeter of either the Doppler or transit time types, particularly during the extracorporeal measurement of blood flow, is diagrammatically illustrated in FIG. 1. This particular embodiment of the hollow flow body (which will be further shown in FIGS. 2 and 3), and still other particular embodiments that will be further shown in various views in FIG. 4 and FIGS. 7 through 10, all appear substantially identical to their exterior, and are all substantially as shown in FIG. 1.

Figure 2A:
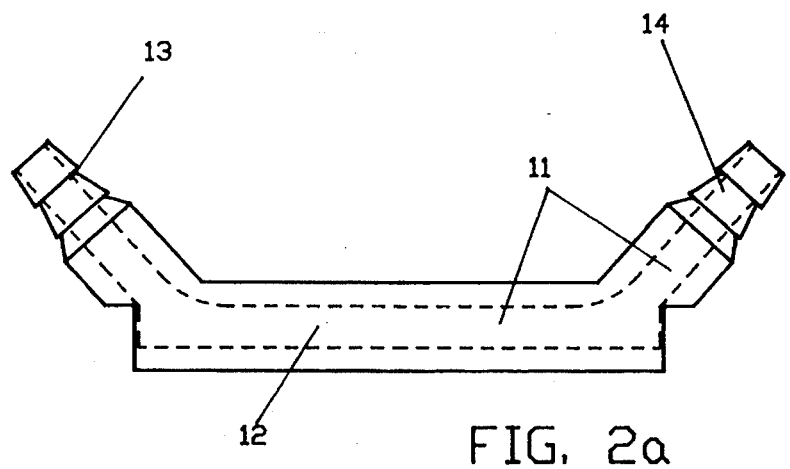
FIG. 2, consisting of FIG. 2a and FIG. 2b, is a side, and an end, cross-sectional view showing one embodiment of the interchangeable disposable flow body of the present invention, having and defining the ultrasonic flow chamber, that was previously seen in FIG. 1.
Figure 2B:
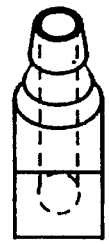

The interchangeable disposable flow body 1 in accordance with the present invention defines an internal flow path 11 including an elongate ultrasonic chamber 12, as is best seen in dashed line within detail FIGS. 2a and 2b. The interchangeable disposable flow body 1 has two flow connectors, or nozzles 13 and 14, located at the opposite ends of its flow path 11. It is through these nozzles 13, 14 that the flow body 1 connects to respective conduits 20, 21 (shown in phantom line for being part of the environment of the present invention) flowing a fluid (not shown) in either direction under force of pump 22 (shown in phantom line). When the flow body 1 is used during the extracorporeal measurement of blood flow then the conduits 20, 21 are normally plastic surgical hoses, and the fluid (not shown) flowing in the conduits 20, 21, and also in the internal flow path 11 of the flow body 1, is fluid blood. In this case the conduit 21 normally connects at still further points along its path to a PUMP 22, and still further to the circulatory system of a living patient, or PATIENT LOAD 23.

A valve (not shown) may be located anywhere in the conduits 20, 21, and may serve to either (i) block and/or (ii) divert fluid flow through the conduits. For example, a diverter valve (not shown) in a one of the conduits 20, 21 flowing fluid from the PATIENT LOAD 23 may serve to empty spent blood into a reservoir while a source of fresh blood is connected, normally downstream from the flow body 1, to the other of the conduits 20, 21 that is flowing fluid into the PATIENT LOAD 23. Accordingly, it should be understood that the fluid circulation outside the flow body 1 shown in FIG. 1 is exemplary only, and that the purposes of the flow body 1 as will be explained are not dependent upon the precise flows of the fluid flow systems within which it is used.

The flow body 1 also has and presents at least one acoustic connector 15 for acoustically connecting o at least one, and potentially several, external ultrasonic transducer assemblies 30 (shown in phantom line for being part of the environment of the present invention). The acoustic connectors 15 normally occupy a substantial finite area of the exterior surface of the flow body 1. The acoustic connectors 15 are typically in the form of two opposed, spaced parallel, exterior surfaces to the flow body 1. These surfaces are located in line with the elongate axis of, and at opposite ends of, the acoustic chamber 12 (shown in FIG. 2).

The flow body 1 illustrated in FIG. 1 is in the substantial shape of parallelipiped body having (i) a substantially square external cross section and (ii) a substantially circular cross section to its interior acoustic chamber 12. Each of the acoustic connectors 15 is a surface in the substantial shape of a square. The acoustic connectors 15 are neither special protuberances nor special plug fittings, but simply regions that come directly into contact with the ultrasonic transducer assemblies 30. These regions serve to acoustically connect the transducers 301 (shown in FIGS. 3,4,9 and 10) of the transducer assemblies 30 with the flowing fluid within the acoustic chamber 12. It is the flow of this fluid (not shown) that is sensed by transducer 301 of the transducer assemblies 30.

The acoustic connectors 15 preferably ultrasonically connect to the one or more transducer assemblies 30 by aid of a mechanism 40 that is external to both the acoustic connectors 15, and to the flow body 1 for which the acoustic connectors 15 are but exterior surfaces. The mechanism 40 serves to clamp, or force, the one or more transducer assemblies 30 and a corresponding one of the acoustic connectors 15 into pressured contact. This necessary tight contact may alternatively be made by other means, such as by gluing or cementing the transducer assemblies 30 to the acoustic connectors 15, preferably temporarily so gluing or cementing.

One preferred mechanism 40 of simple form is shown in FIG. 1. An elongate member 41 substantially in the shape of a parallelipiped body has and presents an elongate interior cavity 42 with an elongate side opening 43. Typically two opposed slots 44 are typically, but not necessarily, located on those two sides of the body member 41 that are perpendicular to the side opening 43. A slide bar 45 is retained for sliding movement within body member 41 under force of spring 46 by action of the slots 44.

During the pressured connection of the acoustic connectors 15 (part of the flow body 1) to the transducer assemblies 30, the slide bar 45 is temporarily pulled by force of the fingers (not shown) against the spring 41, increasing the unobstructed length of the elongate cavity 42 and its elongate side opening 43. The portion of the flow body 1 presenting the ultrasonic connectors 15 is slid, or plugged, into the elongate cavity 42. The elongate cavity 42 presents a complimentary fit in both shape and size to the flow body 1 and to its acoustic connectors 15 (which are normally but simple surfaces). The slide bar 45 is then released, and the force of the spring 41 force biases in position the acoustic connectors 15, and the entire flow body 1 of which the acoustic connectors 15 are a part, firmly against the transducer assemblies 30. The acoustic connectors 15 and the transducer assemblies 30 are thereafter held in pressured contact. Extraction of the acoustic connectors 15, and the entire flow body 1, from the cavity 42 of mechanism 40 may be accomplished simply by reversing the pulling and the plugging process.

The one or more ultrasonic transducer assemblies 30 are electrically connected by wires 31 to an ACOUSTIC FLOWMETER 32 (all shown in phantom line for being part of the environment of the present invention). If a single ultrasonic transducer assembly 30 is used then the ACOUSTIC FLOWMETER 32 is necessarily of the Doppler ultrasonic type. It will, however, be recognized by a practitioner of the mechanical arts that two ultrasonic transducer assemblies 30 could be positioned at each end of the elongate central cavity 42 of mechanism 40, and that both such transducer assemblies 30 could simultaneously be positioned, and thereafter held, in pressured contact with (opposite end surfaces of) the acoustic connectors 15 under force of spring 46. Ultrasonic acoustic connection in accordance with this concept (which will be made increasingly clear in FIGS. 3–7) permits the electrical connection of the ACOUSTIC FLOWMETER 32 via wires 31 to each of two ultrasonic transducer assemblies 30. In such a case the ACOUSTIC FLOWMETER 32 could be (but is not mandated to be) of the transit time ultrasonic acoustic type. It is possible to simultaneously acoustically connect still further ultrasonic transducer assemblies, in numbers greater than two at one time, by extension of the same principles.

An exemplary ACOUSTIC FLOWMETER 32 of the Doppler ultrasonic type is the Model 100 Pulsed Doppler Velocimeter available circa 1994 from Trink Technology, Inc., 4616 Santa Fe Street, San Diego, Calif. 92109, U.S.A. An exemplary ACOUSTIC FLOWMETER 32 of the transit time ultrasonic type Model Number 206 available circa 1994 from Triton Technology, Inc. (assignee of the present invention), 4616 Santa Fe Street, San Diego, Calif. 92109, U.S.A.

Figure 3:
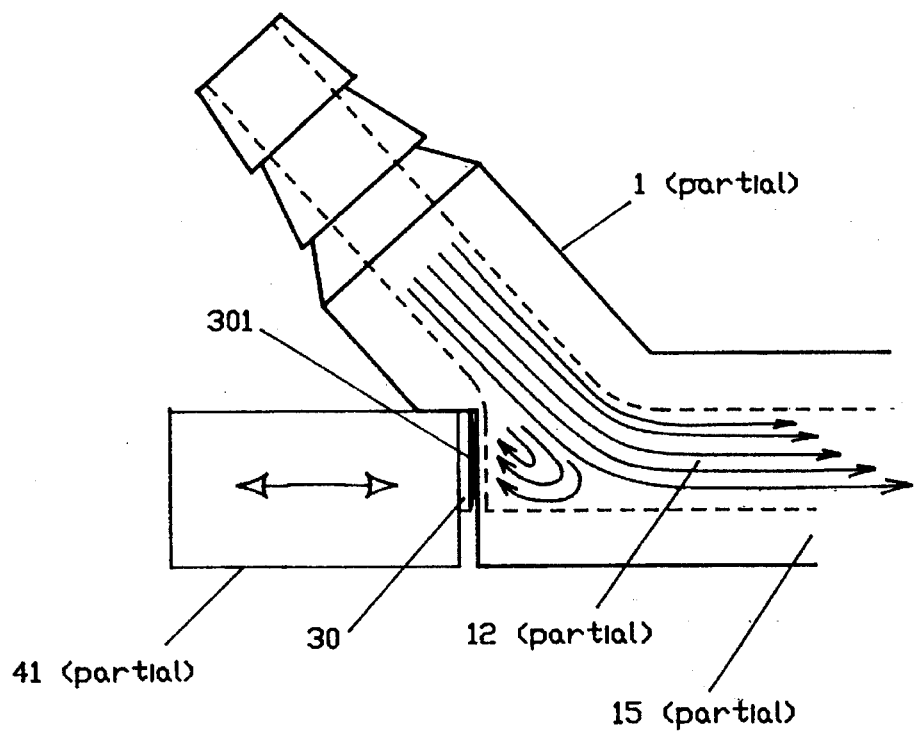
FIG. 3 is a detail view at an enlarged scale of the mating surfaces of that embodiment of the interchangeable disposable flow body previously seen in FIG. 3; this particular alternative embodiment of the interchangeable disposable flow body being shown pre-positioned for use disposed in spatial relationship with an external ultrasonic transducer.
Figure 4:
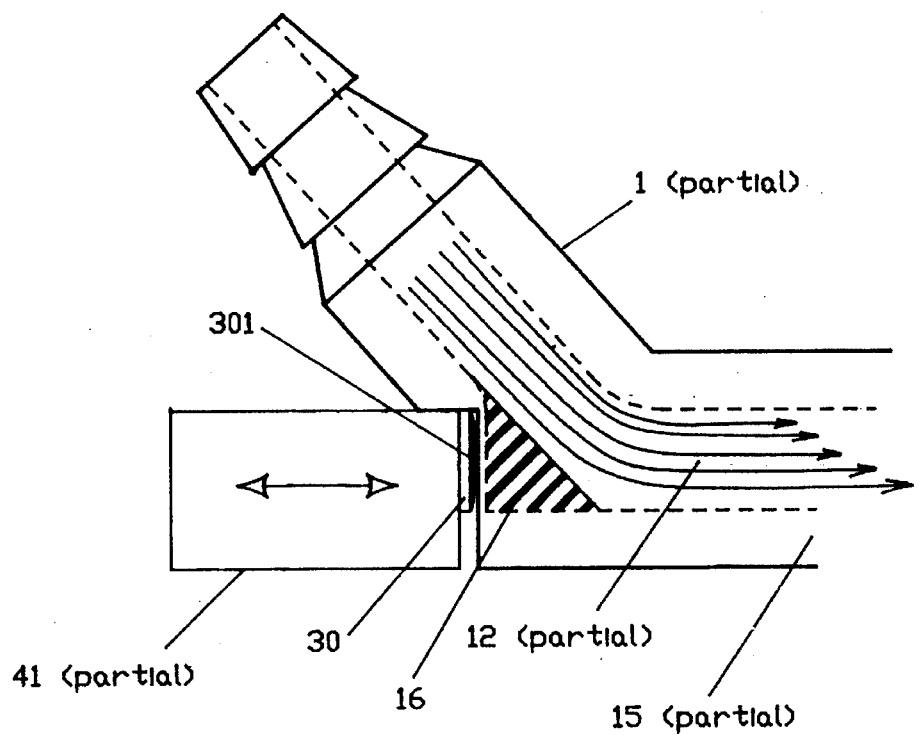
FIG. 4 is a detail view at an enlarged scale of the mating surfaces of another, preferred, embodiment of the interchangeable disposable flow body in accordance with the present invention, this embodiment differing from the embodiment previously seen in FIGS. 2 and 3 by incorporating an acoustic-coupling element in the shape and form of a small wedge located within the flow body so as to form a wall of its interior flow chamber.

Referencing now FIGS. 2 through 4, the path 11 of fluid flow within the flow body 1 can be made as smooth, and as free from obstructions, as is desired. Such minor bends and angles as are observable in the embodiment of FIGS. 2 and 3 are in most cases not appreciably harmful to any of the blood, the blood flow, or the process or accuracy of ultrasonic blood flow measurement. It should be understood that these angular bends, and surfaces, exist so that ultrasound transmitted in acoustic path to and from the flowing blood may pass through the interior walls of the acoustic chamber 12 without substantial refraction. The ultrasound does so pass if these walls to the acoustic chamber 12 are perpendicular to the acoustic vector (not shown in FIGS. 2–4, shown in FIGS. 9 and 10).

However, the existence of angular bends in the walls of acoustic chamber 12 of the flow body 1—normally such as are prone to occur only in regions of the flow chamber 12 that are proximate to the transducers 30—can cause small eddies, or back-flows, in the blood flow along path 11, as is best shown in FIG. 3. These small eddies or whirlpools of blood that form near the non-smooth, angular, features of the acoustic chamber 12 may undesirably induce damage to the blood cells or, in extreme conditions, blood clots. Accordingly, there is a problem in making the interior walls of the acoustic chamber 12 to be smooth and featureless, as is desired for blood flow, without also making them to be, at least in portions, oblique to the vector of acoustic propagation, and causative of undesirable acoustic signal refraction and loss.

In accordance with the present invention a ramrod straight, substantially non-refracting, acoustic path through the flow body 1 and its acoustic chamber 12 may be realized nonetheless that the flow path 11 through the same chamber 12 is very gently bending, and devoid of sharp angular bends angular surfaces. Referencing FIGS. 4 and 7–10, the present invention solves these contradictory requirements by the optional use of one or more acoustic-coupling elements, or acoustic transformers, 16–19. The acoustic-coupling elements 16–19 are positioned (as respectively shown in FIGS. 4,7; 8, 9 and 10) substantially inside the respective flow bodies 1, 1000, 1001, 1002. They may be molded in situ by a two-step process during the fabrication of the flow bodies 1, 1000, 10001, 1002, or they may be inserted along the path 11 into the acoustic chamber 12 and permanently glued in position.

The optional acoustic-coupling elements 16–19 are clearly located in positions so as to form portions of the walls, or backdrops to the walls, of the flow chamber 12. The acoustic-coupling elements 16–19 have the same acoustic impedance as fluid blood, which is a different acoustic impedance that the plastic from which the bulk of the flow body 1 is normally constructed. The acoustic-coupling elements 16–19 are commonly made of cured urethane elastomer, and preferably from ADIPRENE L-100 liquid urethane elastomer available from Uniroyal Chemical Company.

According to the matching acoustic impedance of the acoustic-coupling elements 16–19, an acoustic signal will pass through an interface between one of the acoustic-coupling elements 16–19 and the fluid blood without substantial refraction or reflection regardless of the angle between the acoustic vector and the interface. Accordingly, the acoustic-coupling elements 16–19 substantially solve the challenge of establishing a low-loss, non-refracting, arrow-straight acoustic path through a smooth and bending path of flowing fluid blood within the interior chamber 12 of the respective hollow flow bodies 1, 1000, 1001 or 10002 within which the elements are respectively located.

Figure 9:
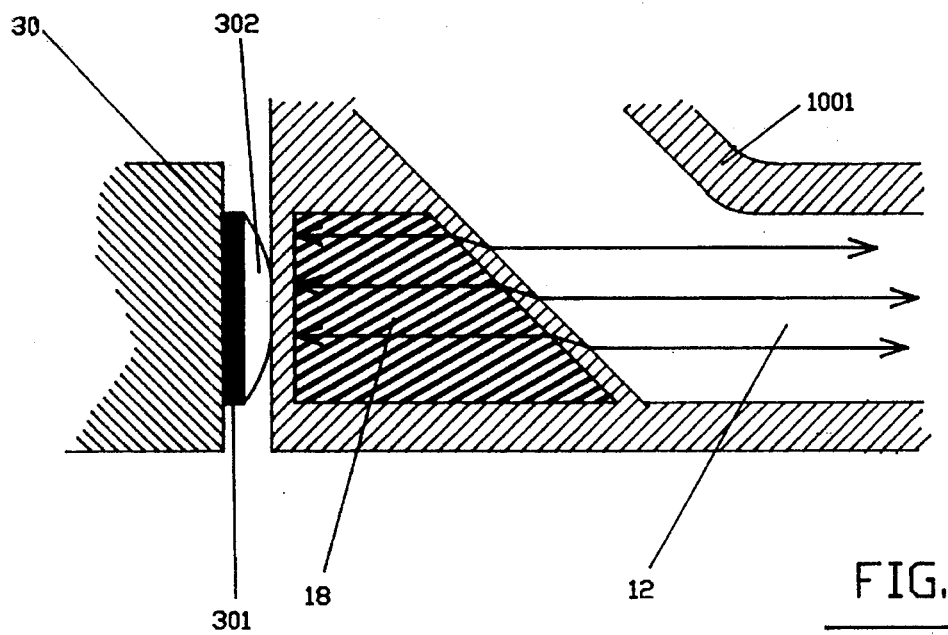
FIG. 9 is a cross-sectional detail view at an enlarged scale of a portion of that embodiment of the interchangeable disposable flow body in accordance with the present invention previously seen in FIGS. 4 and 7, the detail view particularly showing an acoustic-coupling element in the shape and form of a small wedge located within the flow body at a position proximate to a portion of the wall of the flow body's interior flow chamber.
Figure 10:
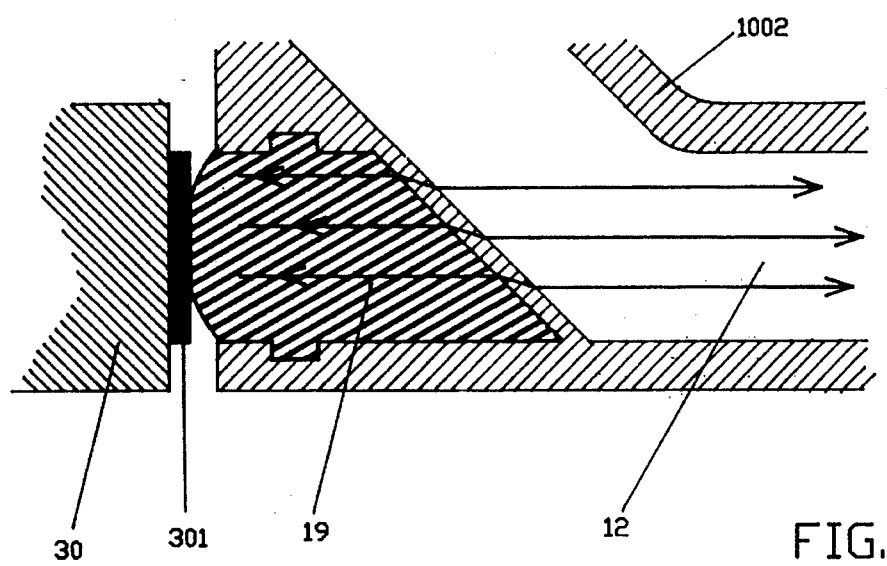
FIG. 10 is a cross-sectional detail view at an enlarged scale, similar to FIG. 9, of yet another embodiment of an interchangeable disposable flow body in accordance with the present invention, this detail view particularly showing an acoustic-coupling element in the shape and form of a small wedge located within the flow body at a position proximate to a portion of the wall of the flow body's interior flow chamber, and exposed at an exterior surface of the flow body so as to directly contact an ultrasonic transducer.

An enlarged detail view of the mating surfaces, or acoustic connectors 15 of the flow body 1, and of the ultrasonic transducer assemblies 30—previously seen in FIG. 1—is shown in FIGS. 3 and 4 (and also, again, in FIGS. 9 and 10). A portion 41 (partial) of the elongate body member 41 of the mechanism 40 is marked with an arrow to show that it moves relative to each of flow body 1 (partial), relative to the surface plane of the acoustic connector 15 (partial), and to relative to the long axis of its elongate acoustic chamber 12 (partial). The ultrasonic transducers 301 are typically thin, planar elements made from ceramic piezoelectric material. The are preferably type LTZ2 available form Transducer Products, Inc., Torrington, Conn., U.S.A. Each ultrasonic transducer 301 is normally permanently affixed to it ultrasonic transducer assembly 30, and the ultrasonic transducer assemblies 30 are in turn semi-permanently affixed to the elongate body member portion 41 (partial), such as by adhesive (not shown). If one ultrasonic transducer assembly 30 fails then it may commonly be replaced at a repair depot without throwing away the other ultrasonic transducer assembly 30, or the clamping mechanism 40. The ultrasonic transducers 301 and the ultrasonic transducer assemblies 30 are not intended to be acoustically coupled to the elongate body member 41 of the clamping member 40 and are, indeed, but very poorly coupled to the elongate body member because of the air gaps supporting the sliding action.

Figure 5:
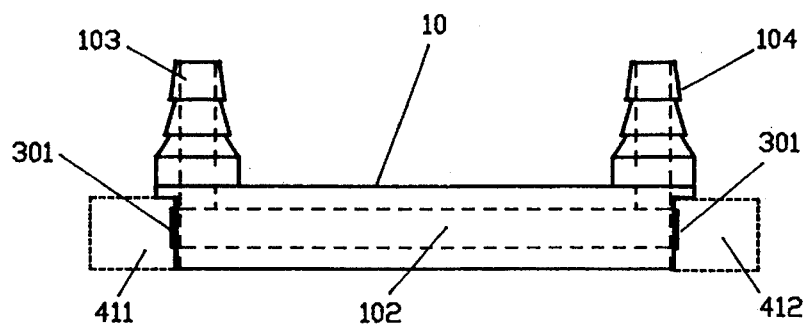
FIG. 5 is a cross-sectional view of yet another alternative embodiment of an interchangeable disposable flow body, which flow body has and presents an ultrasonic flow chamber, in accordance with the present invention; this particular alternative embodiment of the interchangeable disposable flow body being shown pre-positioned for use disposed in spatial relationship with two external ultrasonic transducers.

A cross-sectional view of still another embodiment of an interchangeable disposable flow body 10, having and presenting an ultrasonic chamber 102, is shown in FIG. 5. The flow body 10 is distinguished from flow body 1 (shown in FIGS. 1–4) for having tubing adapters 103 and 104 that are oriented substantially at right angles to, and to the same side of, the long axis of the ultrasonic chamber 102. The flow body 10 is shown pre-positioned for use in a spatial relationship with, and in pressured contact with, two ultrasonic transducers 301, 302. The ultrasonic transducers 301 are pressured into contact with the flow body 10 by relative movement, in the manner of a clamping movement, between the flow body 10 and the portions 411 and 412 of a body member of a mechanism which may be, or which may be similar to, the body member 41 and the mechanism 40 shown in FIG. 1.

Figure 6:
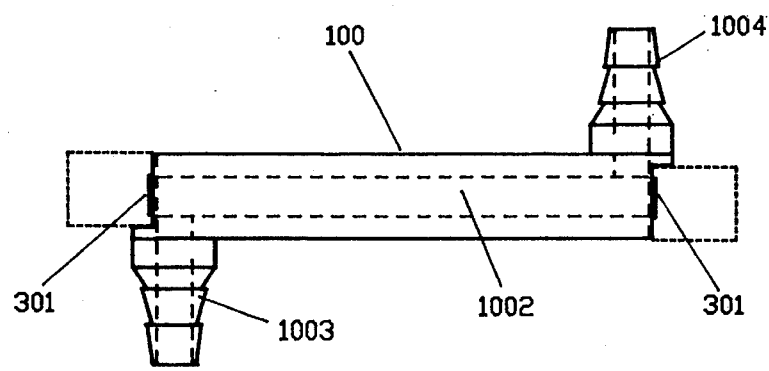
FIG. 6 is a cross-sectional view of still yet another alternative embodiment of an interchangeable disposable flow body, which flow body has and presents an ultrasonic flow chamber, in accordance with the present invention; this particular alternative embodiment of the interchangeable disposable flow body being shown pre-positioned for use disposed in spatial relationship with two external ultrasonic transducers.

A cross-sectional view of still another alternative embodiment of an interchangeable disposable flow body 100, also having and presenting an ultrasonic chamber, is shown in FIG. 6. The flow body 100 is distinguished from flow body 1 (shown in FIGS. 1–4) and flow body 10 (shown in FIG. 5) for having tubing adapters 1003 and 1004 that are oriented substantially at right angles to, and at opposite sides of, the long axis of the ultrasonic chamber 1002. This flow body 100 is again shown pre-positioned for use disposed in spatial relationship with, and in pressured contact with, two ultrasonic transducers 301. Notably, the particular mechanism 40 shown in FIG. 1 will not suffice to accept the flow body 100 shown in FIG. 5. It is, however, a simple task for a practitioner of the mechanical arts to adopt, or configure, a clamping mechanisms to grasp, and to hold, flow bodies of diverse shapes and sizes.

Figure 7:
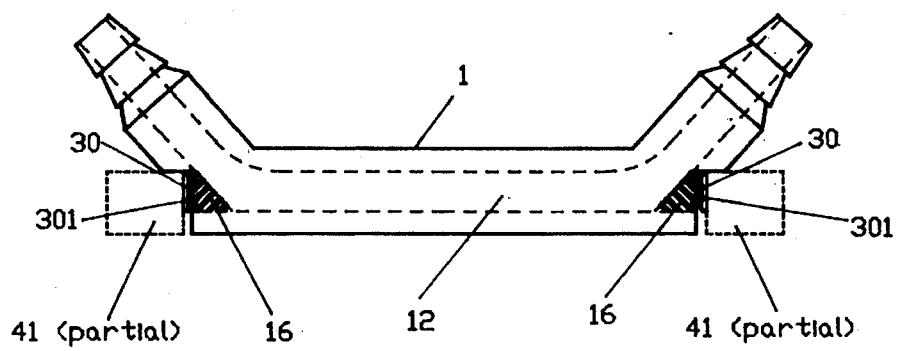
FIG. 7 is a cross-sectional view of that preferred embodiment of an interchangeable disposable flow body, containing an ultrasonic flow chamber and two acoustic-impedance matching bodies, in accordance with the present invention which was previously partially seen in FIG. 4; the flow body now being shown pre-positioned for use disposed in spatial relationship with two external ultrasonic transducers (instead of only that one ultrasonic transducer which the flow body was previously shown to contact in FIG. 4); the flow body incorporating two acoustic-coupling bodies in the shape and form of a small wedges located within the flow body so as to each form a portion of the wall of the flow body's interior flow chamber (as was previously shown in FIG. 4).

A complete cross-sectional view of the embodiment of an interchangeable disposable flow body 1 containing both the ultrasonic chamber 12 and the acoustic-coupling elements 16—previously partially seen in FIG. 4—is shown again in FIG. 7. Now, however, the flow body 1 is now shown pre-positioned for use disposed in spatial relationship with, and in pressured contact with, two ultrasonic transducers 301 of two ultrasonic transducer assemblies 30 instead of just the one ultrasonic transducer assembly 30 previously seen in FIGS. 1 and 2.

The intended showing of FIG. 7 is that the selfsame flow body 1 that, when in contact with only one transducer 301, serves to conduct fluid the flow of which is ultrasonically measured by a Doppler technique may, when contacted by two transducers 301, also serve equally as well to conduct fluid the flow of which is ultrasonically measured by a transit time technique. Ergo, each of the flow bodies 1, 10, 100, 1000, 1001 and 10002—each of which has and defines an ultrasonic chamber 12—in accordance with the present invention is usable with, and during, both Doppler and transit time fluid flow measurement processes.

The same preferred embodiment of an interchangeable disposable flow body—containing an ultrasonic flow chamber and two acoustic-coupling elements—in accordance with the present invention that was previously partially seen in FIG. 4 is shown again in FIG. 7. However, the flow body 1 is now shown pre-positioned for use disposed in spatial relationship with two external ultrasonic transducer assemblies 30 (instead of only that one ultrasonic transducer assembly 30 which the flow body 1 was previously shown to contact in FIG. 4).

The flow body 1 incorporates two acoustic-coupling elements 16 in the shape and form of a small wedges. These wedge-shaped acoustic-coupling elements 16 are located within the flow body 1 in positions so that each forms a portion of the wall of the flow body's interior flow chamber 12 (that was previously shown in FIG. 4).

Figure 8:
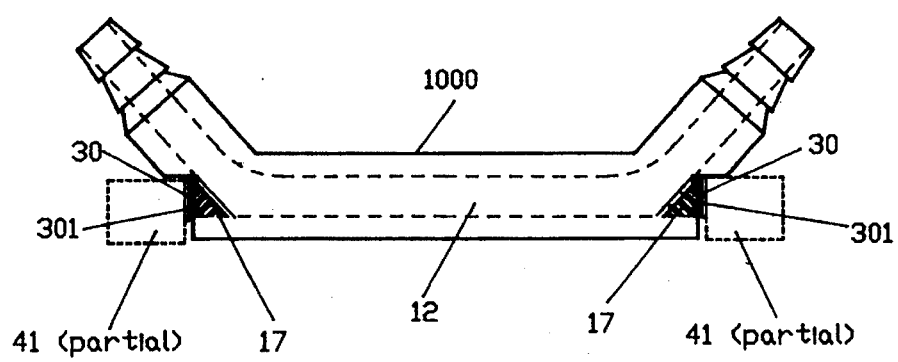
FIG. 8 is a cross-sectional view of yet another preferred embodiment of an interchangeable disposable flow body, containing an ultrasonic flow chamber and two acoustic-impedance matching bodies, in accordance with the present invention; the embodiment shown being similar the embodiment previously seen in FIG. 4 and 7; the embodiment shown being pre-positioned for use disposed in spatial relationship with two external ultrasonic transducers and incorporating two acoustic-coupling bodies each in the shape and form of a small wedge located within the flow body in positions proximate to portions of the wall of the flow body's interior flow chamber.

Yet another preferred embodiment of an interchangeable disposable flow body 1000, containing an ultrasonic flow chamber 12 and two acoustic-coupling elements 17 is shown in FIG. 8. The embodiment of FIG. 8 is similar to the embodiment previously seen in FIG. 4 and 7, however the flow body 1000 is now shown pre-positioned for use disposed in spatial relationship with two external ultrasonic transducer assemblies 30. The flow body 1000 incorporates two acoustic-coupling elements 17 each again having the shape and form of a small wedge. However, instead of directly forming a wall of the chamber 12—as did the acoustic-coupling elements 16 shown in FIGS. 4 and 7—the acoustic-coupling elements 17 are located within the flow body 1000 in positions proximate to portions of the wall of the flow body's interior flow chamber 12.

A portion of that embodiment of the interchangeable disposable flow body in accordance with the present invention previously seen in FIGS. 4 and 7 is shown again in enlarged, detail, view in FIG. 9. An acoustic-coupling element 18 in the substantial shape and form of a small wedge is located within the flow body 1001 at a position proximate to a portion of the wall of the flow body's interior flow chamber 12.

FIG. 9 also illustrates the optional use of an ultrasonic coupling material. For optimal acoustic coupling of the transducers 301 of the ultrasonic transducer assemblies 30 with the flow body 1 when the ultrasonic transducer assemblies 30 are moved into pressured contact therewith, the ultrasonic transducers 301 may optionally be faced with an elastomeric ultrasonic coupling material 302 as shown in FIG. 9. This ultrasonic coupling material 302 may be made from, for example, urethane rubber compound or, alternately, a gel such as Adiprene L-100. The ultrasonic coupling material 302 is normally both compliant and sound-conducting. Although illustrated in FIG. 9 to be located on the exposed face of an ultrasonic transducer 301, it may be located upon either or both the flow body 1001 or on the ultrasonic transducer 301.

Yet another embodiment of an, interchangeable disposable flow body in accordance with the present invention is shown in FIG. 10. Yet another acoustic-coupling element 19—still in the substantial shape and form of a small wedge—is now located within a flow body 1002 at a position proximate to a portion of the wall of the flow body's interior flow chamber 12. This acoustic-coupling element 19 is exposed at an exterior surface of the flow body 1002 so as to directly contact an ultrasonic transducer 301.

In accordance with the preceding explanation, certain modifications and adaptations of the present invention will suggest themselves to a practitioner of the mechanical and/or fluid flow measurement arts. The flow body having the chamber need not be made symmetrical and/or reversible, but could easily be made so as to either (i) flow connect, and/or (ii) ultrasonically connect in but a single directional sense. In other words, the input and output flow tubing adapters need not be the same. In other words, the flow body need not be symmetrical relative to its connection to the one of more transducers and might, instead, fit within a cavity 42 of a mechanism 40 holding one or more transducers in but only a single way, and orientation. In such a manner the direction, and well as the magnitude, of fluid flow could be monitored.

The flow body defining the cavity may be made of clear material so that the flow of fluid, including fluid blood, within the cavity may be visually observed. The flow body may be marked—such as by molding, embossing, printing of labeling—with arrows and other indicia as best suit its positioning, orientation and use. Finally, the flow body in accordance with the present invention could be made with various numbers, and sizes, of flow chambers in order that one disposable flow body could suffice to hold several separate conduits of flowing fluids in contact with a like number of transducers, or transducer pairs, in order that the fluid flow within each of the conduits might be ultrasonically measured.

The engagement of the external ultrasonic transducer(s) with the flow body is normally pressured by spring forces which are developed by the clamping mechanism, and which are thus external to the flow body. It will be recognized by a practitioner of the mechanical arts that the pressure force could be generated by a spring or a compressed elastomer located on the flow body instead of the mechanism. If the flow body were to be of a shape-retentive material, it might be slightly bowed so as to compressively fit within a slightly shorter cavity, therein to be held in pressured contact with the transducer(s). Insuring a tight air-less contact to the flow body.

Likewise, the ultrasonically coupling material facilitating the engagement of the flow body and the transducer(s) need not be located upon the transducer(s), but could, instead, be located upon the flow body.

There requirement for separate acoustic coupling elements 16–19 would be diminished if the entirety of the hollow flow body was of equal acoustic impedance to blood. However, suitably hard surface, durable, economic, moldable and readily sterilized materials also having the acoustic impedance of blood are not know to the inventors.

The design choices made in the preferred embodiment of a flow body having an acoustic chamber in accordance with the present invention seldom represent the sole and only practical, nor even the only inexpensive, alternative to implementing the flow body of the present invention. Instead, the design choices are generally directed to enhancing reliability and safety while maintaining operational simplicity and optimally low cost.

In accordance with the preceding explanation, the present invention should be construed broadly, and in accordance with the following claims only, and not solely in accordance with the embodiments within which the invention has been taught.

What is claimed is:

1. A replaceable fluid flow chamber assembly for a transit time ultrasonic flowmeter that determines fluid flow velocity by a detection of an arrival time shift on ultrasound that is passed through a flowing fluid between a pair of ultrasonic transducers, the assembly comprising:

a flow body having and defining
a smooth and featureless channel therethrough to flow fluid blood without any damaging of blood cells, the flow body and its channel flow connected at both ends of the channel to an external conduit flowing fluid, and
two substantially parallel exterior surfaces located oppositely to each other so that an imaginary line between them will pass through the channel, each of the two surfaces being of a complimentary shape and contour so as to mechanically engage an associated one of the pair of ultrasonic transducers, and each of the two surfaces also having an acoustic impedance suitable to acoustically couple the associated one of the pair of external ultrasonic transducer;
wherein at such times as (i) the flow body's channel is flow connected to the external conduit flowing fluid, and, concurrently, (ii) the flow body's two exterior surfaces mechanically engages and acoustically couples the pair of transducers, then an ultrasonic acoustic path is established between the transducers through the flow body and through the fluid flowing within the flow body's channel;

wherein, by the properties of the transit time ultrasonic flowmeter to determine fluid flow velocity by detecting an arrival time shift on ultrasound that is passed through a flowing fluid between the pair of ultrasonic transducers, the pair of ultrasonic transducers couples ultrasound into the ultrasonic acoustic path and, by detection of the effects on the ultrasound, the ultrasonic flowmeter determines a velocity of fluid flowing within the flow body's conduit, and in the ultrasonic acoustic path between the two transducers and that the channel through the flow body which flows fluid blood without any damaging of blood cells;

wherein fluid flow velocity in the channel of a flow-connected flow body is determinable while that the channel is simultaneously able to flow blood without any damaging of blood cells.

2. The replaceable fluid flow chamber assembly according to claim 1 wherein the flow body further comprises:

two acoustic-coupling bodies each having the same acoustic impedance as a fluid flowing within the flow body and being located in the ultrasonic acoustic path along which the velocity of fluid flow in the flow body's acoustic chamber is sensed by the transit time ultrasonic flowmeter.

3. The replaceable fluid flow chamber assembly according to claim 1 wherein the flow body further comprises:

connection features by which it is manually connected at both ends of its channel to the external conduit flowing fluid.

4. The replaceable fluid flow chamber assembly according to claim 3 wherein at least one of the flow body's connection features comprises:

a nozzle for slipping on an elastomeric hose.

5. The replaceable fluid flow chamber assembly according to claim 1 wherein each of the flow body's two substantially parallel exterior surfaces consists essentially of:

an ultrasonically coupling material that is both compliant and highly sound-conducting to facilitate making a low sound energy loss ultrasonic acoustic connection between the flow body and a corresponding one of the pair of ultrasonic transducers.

6. A replaceable fluid flow chamber assembly for an ultrasonic flowmeter that determines fluid flow velocity by detecting effects on ultrasound that is communicated to a flowing fluid from an ultrasonic transducer, the assembly comprising:

a flow body having and defining a smooth and featureless channel therethrough to flow fluid blood without any damaging of blood cells, the flow body and its channel flow connected at both ends of the channel to an external conduit flowing fluid, and an exterior surface located proximately to the channel, the surface having a complimentary shape and contour to an external ultrasonic transducer so as to mechanically engage the external ultrasonic transducer, and also having an acoustic impedance suitable to acoustically couple the external ultrasonic transducer;

wherein at such times as (i) the flow body's channel is flow connected to the external conduit flowing fluid, and, concurrently, (ii) the flow body's exterior surface mechanically engages and acoustically couples the ultrasonic transducer, then an ultrasonic acoustic path is established through the flow body between the transducer and the fluid flowing within the flow body's channel;

wherein, by the properties of the ultrasonic flowmeter to determine fluid flow velocity by detecting effects on sound that is communicated to a flowing fluid by an ultrasonic transducer, the ultrasonic transducer couples sound into the ultrasonic acoustic path and, by the detection of effects on the sound, the ultrasonic flowmeter determines a velocity of fluid flowing within the flow body's conduit that channel through the flow body which flows fluid blood without any damaging of blood cells;

wherein fluid flow velocity in the channel of a flow-connected flow body is determinable while the channel is simultaneously able to flow blood without damaging blood cells.

7. The replaceable fluid flow chamber assembly according to claim 6 wherein the flow body further comprises:

connection features by which it is manually connected at both ends of its channel to the external conduit flowing fluid.

8. The replaceable fluid flow chamber assembly according to claim 7 wherein at least one of the flow body's connection features comprises:

a nozzle for slipping on an elastomeric hose.

9. The replaceable fluid flow chamber assembly according to claim 7 wherein the flow body's exterior surface consists essentially of:

an ultrasonically coupling material that is both compliant and highly sound-conducting, therein to facilitate making a low-sound-energy loss ultrasonic acoustic connection between the flow body and the ultrasonic transducer.

10. A replaceable fluid flow chamber assembly for an ultrasonic flowmeter that determines fluid flow velocity by detecting effects on ultrasound that is communicated to a flowing fluid from an ultrasonic transducer, the assembly comprising:

a flow body having and defining a smooth and featureless channel therethrough to flow fluid blood without any damaging of blood cells, the flow body and its channel flow connected at both ends of the channel to an external conduit flowing fluid, and an exterior surface located proximately to the channel, the surface having a complimentary shape and contour to an external ultrasonic transducer so as to mechanically engage the external ultrasonic transducer, and also having an acoustic impedance suitable to acoustically couple the external ultrasonic transducer, the flow body's exterior surface consisting essentially of an ultrasonically coupling material that is both compliant and highly sound-conducting to facilitate making a low sound energy loss ultrasonic acoustic connection between the flow body and the ultrasonic transducer;

wherein at such times as (i) the flow body's channel is flow connected to the external conduit flowing fluid, and, concurrently, (ii) the flow body's exterior surface mechanically engages and acoustically couples the ultrasonic transducer, then an ultrasonic acoustic path is established through the flow body between the transducer and the fluid flowing within the flow body's channel;

wherein, by the properties of the ultrasonic flowmeter to determine fluid flow velocity by detecting effects on sound that is communicated to a flowing fluid by an ultrasonic transducer, the ultrasonic transducer couples sound into the ultrasonic acoustic path and, by the detection of effects on the sound, the ultrasonic flowmeter determines a velocity of fluid flowing within the flow body's conduit and that channel through the flow body which flows fluid blood without any damaging of blood cells;

wherein fluid flow velocity in the channel of a flow-connected flow body is determinable while the channel is simultaneously able to flow blood without damaging blood cells.

11. A replaceable blood flow chamber assembly for a ultrasonic flowmeter that determines blood flow velocity by a detection of effects on ultrasound that is communicated to a flowing blood from an ultrasonic transducer, the assembly comprising:

a blood flow body having and defining a smooth and featureless channel therethrough to flow blood without any damaging any blood cells, the flow body and its channel flow connected at both ends of the channel to an external conduit flowing blood, and a first exterior surface located proximately to the channel, the surface having a complimentary shape and contour to an external ultrasonic transducer so as to mechanically engage the external ultrasonic transducer, and also having an acoustic impedance suitable to acoustically couple the external ultrasonic transducer;

wherein at such times as (i) the blood flow body's channel is flow connected to the external conduit flowing blood, and, concurrently, (ii) the blood flow body's first exterior surface mechanically engages and acoustically couples the ultrasonic transducer, then a straight ultrasonic acoustic path is established between the transducer and the blood flowing within the blood flow body's channel;

wherein, by the properties of the ultrasonic flowmeter to determine blood flow velocity by detecting effects on ultrasound that is communicated to flowing blood by an ultrasonic transducer, the ultrasonic transducer couples sound into the ultrasonic acoustic path and, by the detection of effects on the sound, the ultrasonic flowmeter determines a velocity of the blood flowing within the blood flow body's channel and this channel which flows the blood without damaging any blood cells.

12. The replaceable blood flow chamber assembly according to claim 11 for use with a transit time ultrasonic flowmeter where blood flow velocity is determined by a measurement of an arrival time shift of ultrasound that is communicated through flowing blood between a pair of ultrasonic transducers, wherein the blood flow body further has and defines another, second, exterior surface located proximately to the channel and also having a complimentary shape and contour so as to mechanically engage another, second external ultrasonic transducer, and also having an acoustic impedance suitable to acoustically couple the second external ultrasonic transducer;

wherein at such times as (i) the blood flow body's channel is flow connected to the external conduit flowing blood, and, concurrently, (ii) each of the flow body's first and second exterior surfaces acoustically couples a corresponding one of the pair of ultrasonic transducers, then an ultrasonic acoustic path is established between the transducers both through the blood flow body and through the blood flowing within the blood flow body's channel;

wherein, by the properties of the transit time ultrasonic flowmeter to determine blood flow velocity by measuring an arrival time shift on ultrasound that is communicated through flowing blood between a pair of ultrasonic transducers, the ultrasonic transducer couples sound into the ultrasonic acoustic path and, by the detection of effects on the sound, the ultrasonic flowmeter determines a velocity of the blood flowing within the blood flow body's channel, and along the ultrasonic path between the transducers, and this channel which flows the blood without damaging any blood cells.

13. The replaceable blood flow chamber assembly according to claim 12 wherein the blood flow body's second exterior surface is also substantially parallel, and opposite, to the first exterior surface so that an imaginary line between a center of the first surface and a center of the second exterior surfaces will pass through the channel.

14. The replaceable blood flow chamber assembly according to claim 11 wherein the flow body further comprises:

an acoustic-coupling element having the same acoustic impedance as blood flowing within the blood flow body and located in the ultrasonic acoustic path along which path the velocity of blood flow in the blood flow body's acoustic chamber is sensed by the ultrasonic transducer.

15. The replaceable blood flow chamber assembly according to claim 11 wherein the blood flow body comprises:

a first plug connector feature by which the channel of the blood flow body is flow connected to the conduit flowing blood by act of plugging together the conduit and the blood flow body.

16. The replaceable blood flow chamber assembly according to claim 15 wherein the blood flow body comprises:

a second plug connector feature by which the blood flow body is ultrasonically acoustically connected to the at least one ultrasonic transducer by act of plugging together the transducer and the blood flow body;

wherein the blood flow body is completely plug connected in both its blood flow and in its ultrasonic acoustic connections.

17. A replaceable blood flow chamber assembly for a ultrasonic flowmeter that determines blood flow velocity by a detection of effects on ultrasound that is communicated to a flowing blood from an ultrasonic transducer, the assembly comprising:

a blood flow body having and defining a smooth and featureless channel therethrough to flow blood without any damaging any blood cells, the flow body and its channel flow connected at both ends of the channel to an external conduit flowing blood, a first exterior surface located proximately to the channel, the surface having a complimentary shape and contour to an external ultrasonic transducer so as to mechanically engage the external ultrasonic transducer, and also having an acoustic impedance suitable to acoustically couple the external ultrasonic transducer, an adapter by which the channel of the blood flow body is flow connected to the conduit flowing blood by act of plugging together the conduit and the blood flow body, a protuberance having a complimentary shape and size to a cavity of an external body having and defining such a cavity, the at least one ultrasonic transducer being held upon an interior wall of the external body's cavity so that when the flow body's protuberance is plugged into the cavity then the at least one ultrasonic transducer is placed into contact with the blood flow body, by which contact the blood flow body is ultrasonically acoustically connected to the at least one ultrasonic transducer by act of plugging;

wherein the blood flow body is completely plug connected in both its blood flow and in its ultrasonic acoustic connections;

wherein at such times as (i) the blood flow body's channel is flow connected to the external conduit flowing blood, and, concurrently, (ii) the blood flow body's first exterior surface mechanically engages and acoustically couples the ultrasonic transducer, then a straight ultrasonic acoustic path is established between the transducer and the blood flowing within the blood flow body's channel;

wherein, by the properties of the ultrasonic flowmeter to determine blood flow velocity by detecting effects on ultrasound that is communicated to flowing blood by an ultrasonic transducer, the ultrasonic transducer couples sound into the ultrasonic acoustic path and, by the detection of effects on the sound, the ultrasonic flowmeter determines a velocity of the blood flowing within the blood flow body's channel and this channel which flows the blood without damaging any blood cells.

18. The replaceable blood flow chamber assembly according to claim 11 wherein the blood flow body made of sound-conducting material that is essentially sterilizable.

19. The replaceable blood flow chamber assembly according to claim 18 wherein the blood flow body made of sound-conducting material that is disposable.

20. The replaceable blood flow chamber assembly according to claim 19 wherein the blood flow body consists essentially of plastic.

* * * * *